(12) United States Patent
Mantelmacher

(10) Patent No.: US 8,182,546 B2
(45) Date of Patent: May 22, 2012

(54) ATTACHMENT STRAP FOR TRANS-TIBIAL PROSTHETICS

(76) Inventor: H. Lee Mantelmacher, Owings Mills, MD (US)

( * ) Notice: Subject to any disclaimer, the term of this patent is extended or adjusted under 35 U.S.C. 154(b) by 71 days.

(21) Appl. No.: 12/738,717

(22) PCT Filed: May 27, 2008

(86) PCT No.: PCT/US2008/006678
§ 371 (c)(1),
(2), (4) Date: Apr. 19, 2010

(87) PCT Pub. No.: WO2009/051617
PCT Pub. Date: Apr. 23, 2009

(65) Prior Publication Data
US 2010/0211187 A1 Aug. 19, 2010

Related U.S. Application Data

(60) Provisional application No. 60/999,244, filed on Oct. 17, 2007.

(51) Int. Cl.
*A61F 2/78* (2006.01)
*A61F 2/80* (2006.01)
(52) U.S. Cl. ............................. 623/32; 623/33
(58) Field of Classification Search .................... 623/27, 623/31–37, 57
See application file for complete search history.

(56) References Cited

U.S. PATENT DOCUMENTS

| 2,578,019 | A | * | 12/1951 | Ryan | ............................... 623/36 |
| 4,128,903 | A | | 12/1978 | Marsh et al. | |
| 4,149,540 | A | | 4/1979 | Hasslinger | |
| 4,268,922 | A | | 5/1981 | Marsh et al. | |
| 7,713,221 | B1 | * | 5/2010 | Weber et al. | ...................... 602/5 |
| 2007/0232974 | A1 | * | 10/2007 | Serola | ............................. 602/19 |

* cited by examiner

*Primary Examiner* — David Isabella
*Assistant Examiner* — Marcia Hoffman
(74) *Attorney, Agent, or Firm* — Ober, Kaler, Grimes & Shriver; Royal W. Craig

(57) ABSTRACT

A secure anchoring strap over a prosthetic socket for securing a sleeve. The anchoring strap generally comprises a first strap attached at one end to one side of a closed loop buckle. The first strap laden with hook-attachments comprises a woven inner outer material fabric or loop material. A second strap Is attached at one end to another side of the closed loop buckle, the second strap comprising a laden with hook-attachments and a woven Inner outer material fabric or loop material. A user simply wraps the attachment strap around a margin of their sleeve overlying their prosthetic socket, and passes the free end of the first strap back through the closed loop buckle. They pull the opposing free ends of the straps taught, and secure the inner hook-material of the respective straps to the opposing woven fabric beneath, thereby securing the strap tightly in a flush configuration.

9 Claims, 3 Drawing Sheets

ATTACHMENT STRAP FOR TRANS-TIBIAL PROSTHETICS

CROSS-REFERENCE TO RELATED APPLICATIONS

This application is a National Stage of International Application No. PCT/US2008/006678, filed May 27, 2008, which claims the benefit of U.S. Provisional Patent Application No. 60/999,244, filed Oct. 17, 2007, both of which are incorporated by reference.

BACKGROUND OF THE INVENTION (1) Field of the Invention

The present invention relates to prostheses and, more particularly, to an attachment strap for suction sleeves used with trans-tibial prosthetics that allows patients to easily anchor the suction sleeve to the prosthetic.

(2) Description of Prior Art

There are a variety of different types of prosthetic devices for patients that have had either transfemoral (above knee) or transtibial (below the knee) amputations. Typically, post operative prosthetic devices for patients having had either type of amputation begins with a sleeve which is rolled on to the residual limb. The sleeve is a soft, stretchy material that acts as an interface with the prosthesis. Once the sleeve is on, the residual limb then slides into a hard socket. This socket is specially made to fit and can be made out of a variety of materials.

The hard socket for a transfemoral prosthesis has a knee joint connected to it, and the more natural the movement of the knee the better. Transtibial prostheses have no knee joint. In both cases (with or without a knee joint) there typically is an aluminum or carbon fiber tube to which a foot module is connected. There are a number of difficult goals for the design of transfemoral and/or transtibial prostheses (above & below the knee). For one, it is very important that the socket be securely fitted to the limb and secured in place.

Many trans-tibial prostheses rely on suction for a secure hold to the limb. These suction suspensions function by creating a seal between the patient's skin and the prosthesis socket. For transtibial (below-knee) amputees, the simplest method is to apply a rubber-like external knee sleeve (or suction sleeve) over the prosthesis socket that extends from the socket to mid-thigh.

FIG. 1 is a prior art illustration of this suction sleeve 1 applied over a transtibial prosthesis and extending from the socket 3 to mid-thigh. The suction sleeve 1 prevents air infiltration into the prosthesis by serving as a gasket that seals against the skin. The suction sleeve 1 also conforms to the skin and permits the amputee to accommodate changes in residual limb volume by adding or subtracting sock plies.

The suction sleeve 1 may be made of latex, neoprene or fabric-bound silicon gel, in most all cases with some fabric (cotton or Polyester™ weave) outer shell. The suction sleeve 1 fits over the upper lip of the prosthesis socket (around the outside), and is unrolled up and over the knee and thigh areas. The suction sleeve 1 does not actually contact the amputation stump. Typically, the suction sleeve 1 is attached around the outside of the prosthesis socket using some form of pressure sensitive tape 2. Unfortunately, such tape 2 tends to bunch the sleeve on both sides of the tape. This bunched look has a high unsightly profile, and tends to show even under a pants leg. Patients seek a more trim and clean attachment that does not protrude. Moreover, stretch tape tends to shift around during the day, and the tape is more difficult to apply. It also leaves an unsightly adhesive residue that can stain clothing.

It would be greatly advantageous to provide a low-profile attachment strap for more secure attachment of a suction sleeve (or any other prosthetic sleeve) around the outside of a prosthesis socket.

SUMMARY OF THE INVENTION

Accordingly, it is an object of the present invention to provide a low-profile attachment strap for secure attachment of a prosthetic sleeve radially around the outside of the prosthesis socket.

It is another object to provide an attachment strap for secure attachment of a prosthetic sleeve radially around the outside of a prosthesis socket that eliminates bunching of the sleeve.

It is still another object to provide a low-profile attachment strap for secure attachment of a prosthetic sleeve that gives a flat profile even under a pants leg.

It is yet another object to provide a low-profile attachment strap for attachment of a prosthetic sleeve to a prosthetic socket that locks the sleeve in place and will not shift during the day.

It is still another object to provide a low-profile attachment strap that is easy for the patient or clinician to attach and which uses no adhesive, thereby not leaving any adhesive residue.

It is still another object to provide a low-profile attachment strap that is user-adjustable and allows an amputee to install a new sleeve if a hole or tear develops, which would otherwise create a lack of proper suction in the sleeve.

In accordance with the foregoing object, the present device comprises an anchoring strap for securing a sleeve over a prosthetic socket, comprising a first strap attached at one end to one side of a closed loop buckle. The first strap comprises an inner material laden with hook-attachments and a woven outer fabric or loop material. A second strap is attached at one end to another side of the closed loop buckle, the second strap comprising an inner material laden with hook-attachments and a woven outer fabric or loop material. A user simply wraps the attachment strap around a margin of their sleeve overlying their prosthetic socket, and passes the free end of the first strap back through the closed loop buckle. They pull the opposing free ends of the strap taught, and secure the inner hook-material of the respective straps to the opposing woven fabric beneath, thereby securing the strap tightly in a flush configuration.

DETAILED DESCRIPTION OF THE PREFERRED EMBODIMENTS

The present invention is a low-profile attachment strap for secure attachment of a prosthetic sleeve radially around the outside of the prosthesis socket. The attachment strap is particularly suited for securing suction sleeves to the socket of a trans-tibial (below knee) prosthesis with more stability against extraneous up and down motion, pivoting, rotation and shift during ambulation.

Figure 1:
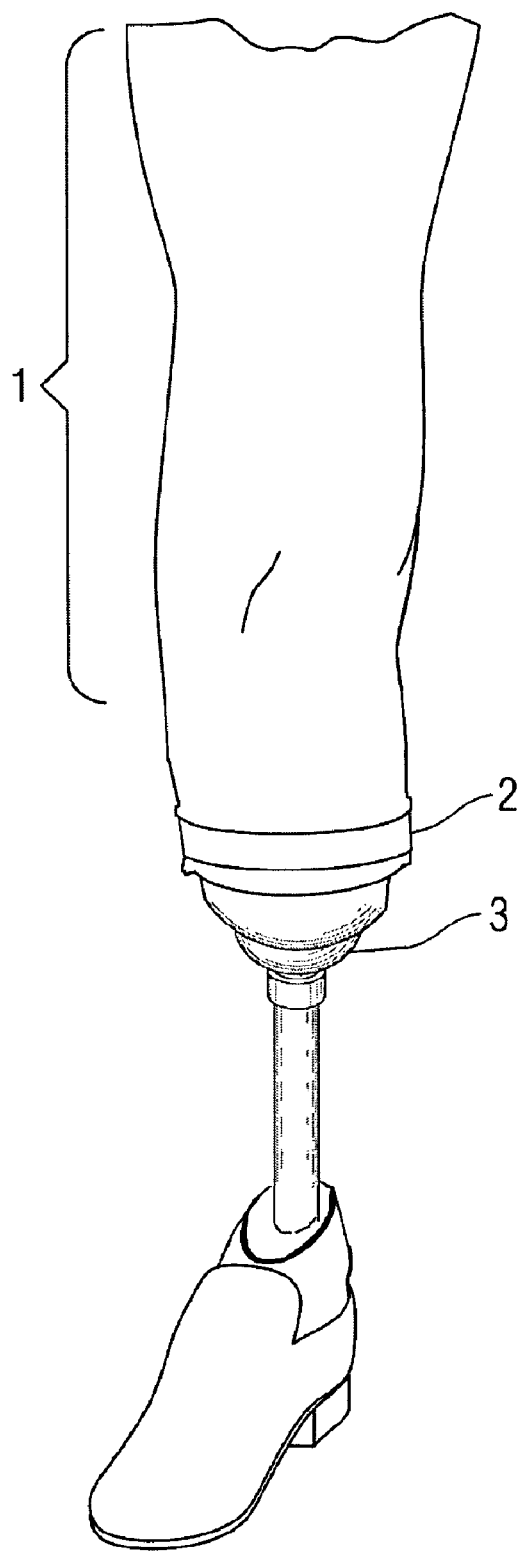
FIG. 1 is a perspective view of a prosthetic sleeve 1 attached radially around the outside of a trans-tibial prosthesis socket 3 by means of a prior art attachment tape 2 which causes bunching and sticky residue.
Figure 2:
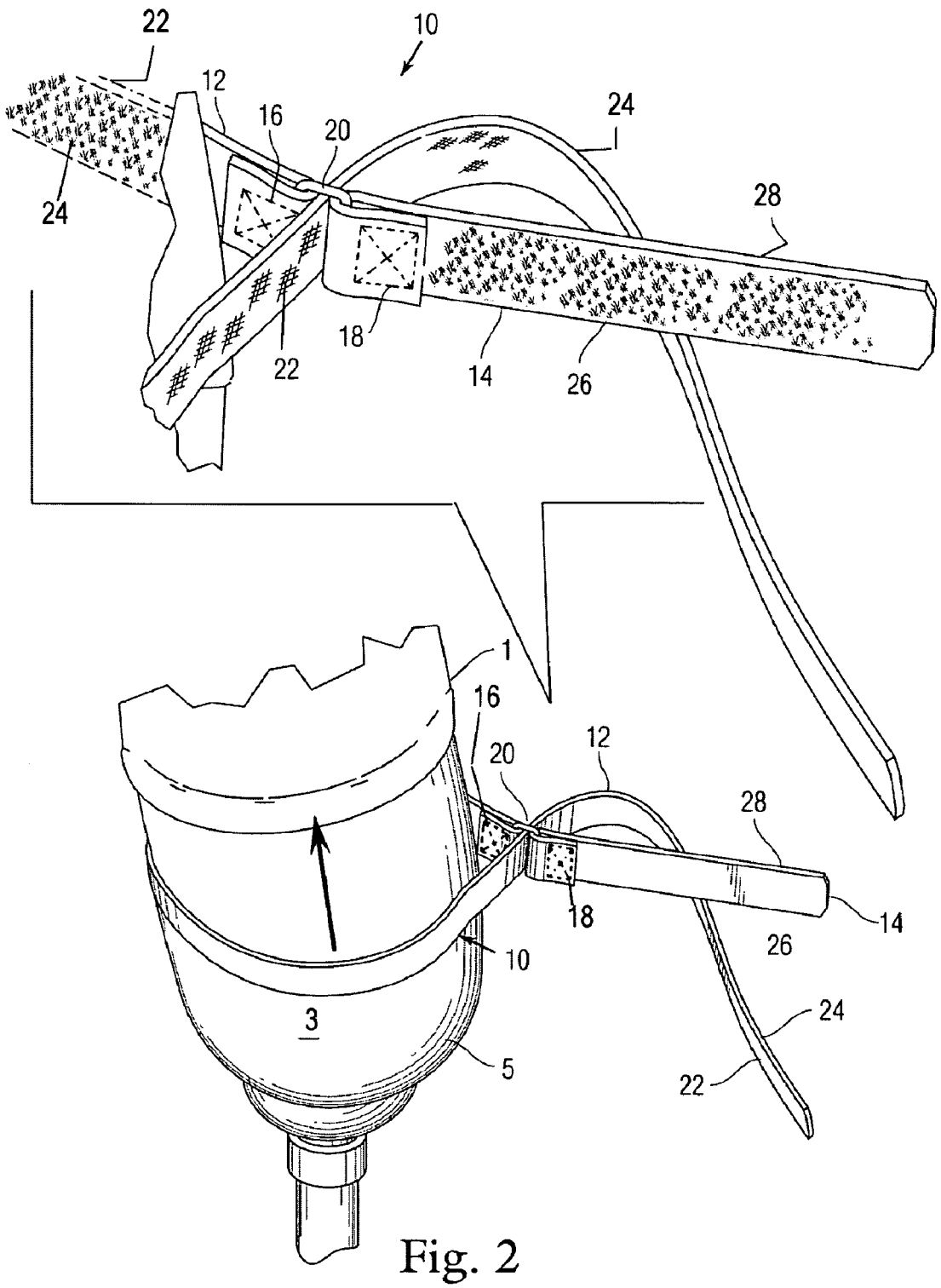
FIG. 2 is a perspective view of a prosthetic sleeve 1 overlying the outside of a trans-tibial prosthesis socket 3 and about to be secured by an attachment strap 10 according to the present invention. An enlarged inset of the attachment strap 10 is also shown.
Figure 3:
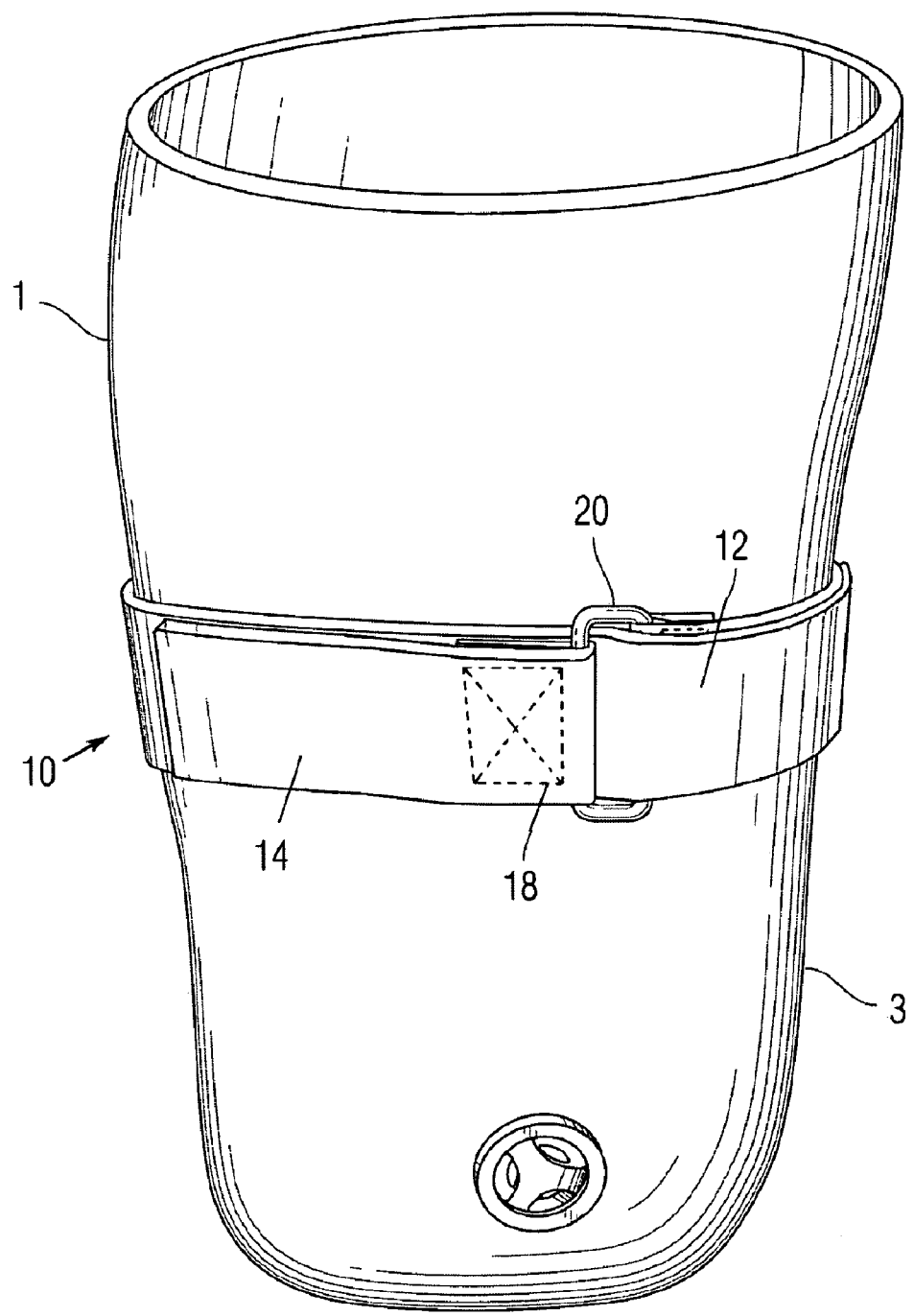
FIG. 3 is a close-up front view of the attachment strap 10 fully securing the prosthetic sleeve 1 around the outside of a trans-tibial prosthesis socket 3.

FIG. 2 (bottom) is a perspective view of a prosthetic sleeve 1 overlying the outside of a trans-tibial prosthesis socket 3 and about to be secured by the attachment strap 10 according to the present invention. An enlarged inset of the attachment strap 10 is also shown (top). The attachment strap further comprises a first strap of elongate webbing 12 passed at one end through a closed loop rectangular buckle 20 (on one side) and secured onto itself by stitching 16, thereby leaving one end of the first strap 12 free. The attachment strap 10 also comprises a second strap of elongate webbing 14 the other side of closed loop buckle 20 and secured onto itself by stitching 18, thereby leaving one end of the second strap 14 free.

The second strap 14 is somewhat shorter than the first strap 12, for example the first strap 12 may be 1.5 feet long and the second strap 8" long.

The closed loop rectangular buckle 20 may comprise any conventional metal or plastic buckle, preferably rectangular to maintain alignment with the opposing straps.

In use, the free end of the first strap 12 is looped around the junction of the sleeve 1 where it overlies the socket 3 and is passed through the closed loop buckle 20. This configuration provides the wearer with the two free ends 12, 14 of the strap 10 to grasp and tighten.

In accordance with the present invention, the inside of the first strap 12 is equipped with inwardly disposed hook material 24 of hook-and-loop nature. This way, when the free end of the first strap 12 is looped around the junction of the sleeve 1 (where it overlies the socket 3) and is tightened it binds to the cloth outer shell of the sleeve 1. The outside of both straps 12, 14 are equipped with loop material 22, 28, respectively, or in the alternative a fabric weave material (cotton or Polyester will suffice) to provide the same benefits as loop material. The inside of the second strap 14 is provided with inwardly disposed hook material 26. This way, the free end of the second strap 14 may be looped back around the exterior of the first strap 12 (which encircles the socket 3) and tightened, whereupon it binds to the cloth (or loop) exterior 22 of the first strap 12. The first strap 12 may be formed by adhering and/or sewing separate straps of loop material 22 and hook material 24 in a back-to-back configuration, and the second strap 12 may be formed by adhering and/or sewing separate straps of loop material 28 and hook material 26 in a back-to-back configuration.

Alternately, there are commercially available straps bearing hook material on one side and loop one the other, in one unitary strap. For example, Velcro USA™ sells this under their VELCRO® brand ONE-WRAP® product line, which are self-gripping fasteners in a back-to-back fastening system. As still another alternative, Velcro USA™ sells under its VELCRO® brand their OMNI-TAPE® brand fastener which is a single component hook and loop fastener having alternating rows of nylon hook and loop on the same surface, and in this instance double-sided OMNI-TAPE® straps can be used for both hook sections 24, 26 and loop sections 22, 28 of both strap straps 12, 14.

In use, a wearer will generally stretch his/her sleeve 1 onto the open end of their prosthetic socket 3 and fold/roll it down over the prosthesis. They insert their limb into the prosthetic socket 3 and unfold/roll the sleeve 1 back up the extent of their thigh, leaving the lower margin of the sleeve 1 overlying the upper rim of the prosthetic socket 3. The attachment strap 10 is wrapped around the overlying section of the sleeve 1, and the free end of the first strap 12 is passed back through the closed loop buckle 20. The wearer then grips each of the two free ends 12, 14 of the strap 10 with their respective hands and pulls taught to tighten, wrapping the free ends back around. When the inside of the first strap 12 is tightened around the sleeve 1 it binds to the cloth outer shell of the sleeve 1. Likewise, when the residual free end of the first strap 12 is pressed against itself the hook interior 24 of the first strap binds to the cloth/loop exterior of the first strap 12, thereby securing the residual end of the first strap 12 in a flush configuration.

Similarly, when the free end of the second strap 14 is looped around the exterior of the first strap 12 (which encircles the socket 3) and is pressed against the first strap 12 it binds to the cloth (or loop) exterior of the first strap 12, thereby securing the second strap 14 in a flush configuration.

By virtue of the binding action of the strap 10 radially around the entire sleeve 1 the strap 10 locks the sleeve 1 in place and will not shift during the day, despite active use. Moreover, since the user is able to grip and pull both free ends of the straps 12, 14 the strap 10 is easy to attach and provides a firm embrace and superior lock without adhesive, thereby not leaving any adhesive residue. Moreover, the binding action of the strap 10 eliminates bunching of the sleeve 1 and presents a flat uniform profile under a pants leg, thereby increasing the aesthetic value of the strap 10. The tightened strap 10 also prevents the sleeve 1 from inverting when the sleeve 1 is rolled down around the prosthetic socket 3.

INDUSTRIAL APPLICABILITY

Post operative prosthetic devices for leg-amputees are often used with a sleeve that is rolled onto the residual limb before application of the prosthetic. The prosthetic is put on, and the sleeve is rolled over the lip of the prosthetic shell. Currently, pressure sensitive tape is adhered thereabout to adhere the sleeve against the socket of the prosthetic, but ad hoc tape tends to bunch the sleeve and it leaves a sticky residue. Patients seek a more trim and secure attachment, and so there is significant industrial applicability in providing a low-profile attachment strap for more secure attachment of a suction sleeve (or any other prosthetic sleeve) around the outside of a prosthesis socket. That is, a user-adjustable attachment strap that allows an amputee to install a new sleeve if a hole or tear develops, which would otherwise create a lack of proper suction in the sleeve.

What is claimed is:

1. In combination with an elastomeric suction sleeve formed with a fabric shell, inserted onto a prosthetic suction socket and adapted to be unfurled up and around a wearer's residual limb to maintain suction in said socket, an improvement comprising an attachment strap for securing said sleeve exteriorly over a rim of said prosthetic socket, said attachment strap further comprising:

a closed loop buckle;

a first flexible strap attached at one end to one side of said closed loop buckle and extending there from to a free end, said first strap comprising an inner hook material laden with hook-attachments covering an entire inside surface of said first strap, and said first strap comprising an outer loop fabric laden with loops covering an entire outside surface of said first strap;

a second flexible strap attached at one end to another side of said closed loop buckle and extending there from to a free end, said second strap comprising an inner hook material laden with hook-attachments covering an entire inside surface of said second strap, and said second strap comprising and an outer loop fabric laden with loops covering an entire outside surface of said second strap, and said second flexible strap being shorter than said first flexible strap;

whereby a user may wrap the first strap around a section of their sleeve overlying their prosthetic socket such that a first length of said first strap is bound by its inner hook material to the fabric shell of said sleeve and a second length of said first flexible strap extending beyond said first length to said free end is not bound to said fabric shell, pass the free end of the first strap back through the closed loop buckle, pull the free end of the first flexible strap apart from the free end of the second flexible strap until both of said first and second flexible straps are taut, bind the inner hook-material along the second length of the first strap to the outer loop fabric along the first length of said first flexible strap, and bind the inner hook material along the second length of the second strap to the outer loop fabric along the first length of the first strap to secure both of said first and second flexible straps tightly in a flush configuration.

2. The attachment strap according to claim 1, wherein said first flexible strap comprises an outer woven fabric laden with loops covering an entire outside surface of said first strap.

3. The attachment strap according to claim 2, wherein said second flexible strap comprises an outer woven fabric laden with loops covering an entire outside surface of said second strap.

4. The attachment strap according to claim 1, wherein said first flexible strap and said second flexible strap both comprises a hybrid of hook attachments and loop fabric on both sides.

5. The attachment strap according to claim 1, wherein said first flexible strap and said second flexible strap both comprises a hybrid of hook attachments and woven fabric on both sides.

6. The attachment strap according to claim 1, wherein said first strap is approximately 8" long and said second strap is approximately 1.5' long.

7. A prosthetic for a residual limb, comprising:
   a prosthetic limb having a suction socket adapted to receive a residual limb;
   an elastomeric suction sleeve having an outer fabric shell, said sleeve being adapted for insertion over the suction socket of said prosthetic limb and adapted to be unfurled up and around said residual limb for covering a portion of said residual limb and a rim of said suction socket in order to maintain suction within said suction socket;
   an attachment strap for securing said sleeve over the rim of said socket, said attachment strap further comprising a closed loop buckle, a first flexible strap attached at one end to one side of said closed loop buckle and extending there from to a free end, said first strap further comprising a releasable attachment fabric formed with a hybrid of hook and loop fasteners covering an entirety of both inner and outer sides of said first flexible strap, and
   a second flexible strap attached at one end to another side of said closed loop buckle, said second strap comprising a releasable attachment fabric formed with a hybrid of hook and loop fasteners covering an entirety of both inner and outer sides of said second flexible strap, and said second strap being shorter than said first strap;
   whereby a user may wrap the first strap of said attachment strap around a section of said suction sleeve overlying said suction socket such that a first length of said first strap is bound by said inner side releasable attachment fabric to the fabric shell of said suction liner and a second length of said first strap extends beyond said first length to said free end is not bound to said fabric shell, pass said free end of the first strap back through the closed loop buckle, pull the free end of the first flexible strap apart from the free end of the second flexible strap until both of said first and second flexible straps are taut, bind the inner side releasable attachment fabric along the second length of the first strap to the outer side releasable attachment fabric along the first length of said first flexible strap, and bind the inner side releasable attachment of the second strap to the outer side releasable attachment fabric along the first length of the first strap to secure both of said first and second flexible straps tightly in a flush configuration.

8. The attachment strap according to claim 7, wherein said releasable attachment fabric comprises a hybrid hook-and-loop material.

9. The attachment strap according to claim 7, wherein said first strap is approximately 8" long and said second strap is approximately 1.5' long.

* * * * *